(12) United States Patent
Jeyanandarajan (10) Patent No.: US 9,427,224 B1
(45) Date of Patent: Aug. 30, 2016

(54) APPARATUS AND METHODS FOR SURGICAL ACCESS

(71) Applicant: Dhiraj Jeyanandarajan, Irvine, CA (US)

(72) Inventor: Dhiraj Jeyanandarajan, Irvine, CA (US)

(*) Notice: Subject to any disclaimer, the term of this patent is extended or adjusted under 35 U.S.C. 154(b) by 372 days.

(21) Appl. No.: 14/120,378

(22) Filed: May 14, 2014

Related U.S. Application Data

(60) Provisional application No. 61/823,338, filed on May 14, 2013.

(51) Int. Cl.
*A61B 17/02* (2006.01)
*A61B 5/00* (2006.01)
*A61B 17/00* (2006.01)

(52) U.S. Cl.
CPC ......... *A61B 17/0218* (2013.01); *A61B 5/4836* (2013.01); *A61B 5/4893* (2013.01); *A61B 2017/00026* (2013.01); *A61B 2017/00115* (2013.01)

(58) Field of Classification Search
CPC .................. A61B 17/0218; A61B 5/4893
See application file for complete search history.

(56) References Cited

U.S. PATENT DOCUMENTS

| 7,282,033 B2 * | 10/2007 | Urmey | A61B 5/05 600/554 |
| 9,358,385 B2 * | 6/2016 | Jenks | A61N 1/0502 |
| 2009/0209879 A1 * | 8/2009 | Kaula | A61B 5/0488 600/546 |

* cited by examiner

*Primary Examiner* — Andrew Yang
(74) *Attorney, Agent, or Firm* — William A. English; Vista IP Law Group LLP (57) ABSTRACT

Apparatus, systems, and methods are provided for performing assessments while doing surgery using evoked potential somatosensory and/or magnetic field induction to determine the proximity and/or location of nerves relative to surgical instruments when accessing a surgical target site.

19 Claims, 6 Drawing Sheets

Step 1
Stimulating surface or needle electrodes attached to the patient at defined points that correspond with nerves that have pathways which pass in or near the surgical zone

Step 2
Using the surgical apparatus as a measuring device to record evoked responses off the stimulated nerves at a site proximal to the stimulation site.

Step 3
Determine the relationship between the surgical accessory and the nerve based on the measured response in step 2.

Step 4
Communicating the relationship determined in step 3 to the user.

Step 5
Using the surgical apparatus as a stimulating device to activate motor nerves in proximity to the apparatus.

Step 6
Recording electromyographic responses induced by step 5.

Step 7
Combining information from steps 3, 5 and 6 to provide a detailed map of both sensory and motor nerves in proximity to the surgical apparatus.

APPARATUS AND METHODS FOR SURGICAL ACCESS

RELATED APPLICATION DATA

This application claims benefit of provisional application Ser. No. 61/823,338, filed May 14, 2013, the entire disclosure of which is expressly incorporated by reference herein.

FIELD OF THE INVENTION

The present invention relates to apparatus and methods for surgery. More particularly, the present invention is directed to a device that uses neurophysiological signals to determine the location of a surgical device relative to nervous tissue.

BACKGROUND

A number of surgical techniques and approaches involve establishing a working channel to gain access to a target site of surgical interest. Depending on the anatomical location of the surgical target site and the approach, the instruments required for the surgery may pass near nervous system structures, which in turn can be damaged if contacted by the surgical instruments. Examples of different surgical fields where this may be an issue include spinal, urological, vascular, and cardiothoracic surgery.

Currently, there are systems that attempt to provide neurophysiological monitoring to help reduce the risk of nerve or other damage by creating a stimulating current from a surgical device. This current, in turn, stimulates any nerves that are in close proximity to the surgical device. If these nerves have a motor component, this stimulating current then activates the nerve and the impulse travels downstream to a muscle group and activates that muscle. Surface or needle electrodes that are in or near the muscle that is activated can pick up the electrical activity generated by the muscle twitch. This process of recording electrical activity generated by contracting muscles is called electromyography (EMG).

During some types of minimally invasive spinal surgery, dissection and dilation through the iliopsoas muscle places the lumbosacral plexus at risk for mechanical injury, particularly at the L4-L5 level, as the position of the nerve root is more anterior compared with the upper lumbar levels. Serious approach related complications from the transpsoas technique occur frequently and are likely underreported. Literature review suggests several case reports with adverse outcomes resulting in transient or permanent motor deficits as a result of nerve damage. This is occurring even with the current systems of neurophysiological monitoring and improved systems would certainly be beneficial.

Therefore, apparatus and methods for guiding and/or manipulating surgical instruments relative to nervous tissue would be useful.

SUMMARY

The present invention is directed to apparatus and methods for performing surgical procedures and assessments, including the use of neurophysiology-based monitoring to determine nerve distance and/or location in three dimensional space relative to surgical instruments employed in accessing a surgical target site.

Evoked potential monitoring may be used to test the integrity of the nervous system. A stimulus current may be delivered to a peripheral nerve, the impulse travels from the peripheral nervous system to the central spine and brain. Recording this signal as it passes by various established points provides the basis for somatosensory evoked potential monitoring. The apparatus and methods herein may include a probe as a recording device either standalone or in combination with stimulating function to provide greater resolution of the proximity of the device to surrounding nerves. This is a novel approach to the existing systems that utilize EMG alone for nerve detection.

The apparatus and methods herein may accomplish this by combining neurophysiological monitoring of evoked nerve responses with one or more instruments used in or in preparation for surgery (referred to herein as "surgical accessories"). By way of example only, such surgical accessories may include, but are not necessarily limited to, any number of devices or components for creating an operative corridor to a surgical target site such as K-wires, sequentially dilating cannula systems, distractor systems, and/or retractor systems. Although described herein largely in terms of use in spinal surgery, it will be appreciated that the apparatus and methods herein are suitable for use in any number of additional surgical procedures wherein tissue having significant neural structures must be passed through (or near) in order to establish an operative corridor to a surgical target site.

In an exemplary embodiment, a method for surgical access is provided that includes: (a) stimulating one or more electrodes on a surgical apparatus to activate peripherally located nerves in generally defined distribution patterns that correspond with nerves passing near or through the site of surgical access as the activated nerve signal follows its physiologic pathway from the periphery to the central nervous system (spinal cord); (b) measuring the electromagnetic signals generated by the nerve(s), e.g., through recording sensors on the surgical apparatus itself; and (c) determining a relationship between the nerve(s) and the surgical accessory based on the responses measured in step (b). In addition, optionally, the method may also include (d) stimulating electrodes on the surgical apparatus that allow the user to stimulate the motor component of nerves in proximity to the surgical apparatus by the current that travels through the natural path of the motor nerve to its target muscle; and (e) using recording electrodes at the target muscle site to pick up the electrical activity generated by the triggered muscle contraction. In addition, the method may include (f) communicating the relationship obtained by one or both of steps (a)-(c) and (d)-(e) to the surgeon in an easy to interpret fashion, e.g., on a display or other output device. In order to improve the resolution of the anatomical location, nerves and/or other key anatomical landmarks such as bone, blood vessels, muscles, fat, and the like may be identified and included in the information presented to the surgeon. For example, the method may utilize data from radiographic imaging studies (e.g., computed tomography, X ray, magnetic resonance imaging) or other navigation devices, and present such information on a display in conjunction with the locational relationship information.

The step of stimulating may be accomplished by applying any of a variety of suitable stimulation signals to the peripheral extension of the nerves of interest that may pass near the surgical apparatus during introduction into the patient's body. The nerves may be stimulated by either surface or needle electrodes, e.g., corresponding to a dermatomal distribution of sensory nerves or the activation of mixed nerves commonly used for evoked potential monitoring (including by way of example, but not limited to, the tibial, sural, and/or femoral nerve). In addition to or instead of electrical stimulation, the nerves may be stimulated by thermal, mechanical, magnetic, and/or any stimulation method that elicits an action potential in the underlying nerve.

The step of measuring the response of nerves innervated by the stimulation step may be accomplished by one or more recording sensors carried by the surgical apparatus that may detect electrical and/or magnetic properties of the nerve(s) that are in proximity to the surgical apparatus. Any variety of recording sensors that detect changes in the electrical potential, electrical current, and/or magnetic field may be provided on the surgical apparatus to measure relevant parameters such as voltage, current flow, and/or magnetic fields.

The step of determining the relationship between the surgical apparatus and the nerve(s) based upon the measurement step may be performed in any number of suitable fashions that provide the proximity in three dimensional coordinates of the nerve(s) relative to the surgical apparatus. In addition, the apparatus may interface with imaging studies (e.g., computed tomography, magnetic resonance imaging, x-ray, or similar studies) either performed before or during the surgical procedure, e.g., to provide more detail to the anatomical relationship of other internal body structures to the surgical apparatus and the nerve responses the surgical apparatus is measuring.

Optionally, the step of stimulating nerves at the surgical site may be accomplished by stimulating electrodes built into or otherwise carried by the surgical apparatus. The current generation of the stimulating electrodes may be user-adjusted for pulse width, intensity, and/or repetition pattern, e.g., to maximize the stimulus response in the motor component of the nerve roots in proximity to the surgical apparatus.

The step of recording the electromyographic response from muscles activated by the stimulation of the motor component of the nerves may be accomplished by recording electrodes. These recording electrodes pick up the electrical activity generated by the muscle when the muscle contracts. The electrical representation of that contraction is called a compound muscle action potential. Recording electrodes may either be surface electrodes placed on the skin surface overlying muscles or they may be needle electrodes inserted into the muscle itself. The electrical muscle activity picked up by the electrodes may be communicated to an amplifier and/or processor, e.g., to obtain the optimal signal. This step may be achieved by any number of suitable algorithms. By way of example only, one such algorithm for motor nerve activation and detection of distance and direction is disclosed in U.S. Publication No. 2012/0220891, the entire disclosure of which is expressly incorporated by reference herein. There may be advantages in combining recording sensors on a surgical apparatus (measuring nerve response from remote stimulating electrodes) with also providing stimulating electrodes on the surgical apparatus, e.g., using the algorithms disclosed in U.S. Publication No. 2012/0220891, e.g., to increase the sensitivity and/or specificity of the distance measurement and/or direction detection.

The step of communicating the relationship of the sensory and motor nerves to the surgeon in an easy-to-interpret fashion may be accomplished in any number of suitable fashions, including but not limited to the use of alphanumeric characters or graphics on a digital display, audio and tactile feedback, and/or other methods that serve to clearly depict the relation of the surgical apparatus to the nerves and/or other anatomical structures visible on imaging studies.

In accordance with an exemplary embodiment, a system is provided for forming an access path through tissue in a patient's body that includes an elongate shaft comprising a proximal end, a distal end sized and configured for introduction into a patient's body to create an access path through tissue, a first plurality of stimulating elements movable on the shaft and configured to contact skin of the patient's body into which the shaft is introduced, and a plurality of sensors fixed on the shaft and spaced apart from one another between the proximal and distal ends. Optionally, the system may also include a second stimulating element configured to be coupled to a patient's body to deliver stimulating energy to one or more nerves within the patient's body.

A controller may be coupled to the first plurality of stimulating elements for delivering first stimulating energy signals to the first plurality of stimulating elements and, optionally, coupled to the second stimulating element for delivering second stimulating energy signals to nerves within the patient's body. The controller may also be coupled to the sensors for detecting signals from the first and/or second stimulating elements passing through tissue within which the shaft is inserted to determine a spatial relationship between the shaft and nerves within the patient's body activated by the second stimulating energy signals. The system may also include an output device, e.g., a display, for presenting information related to the spatial relationship between the shaft and the nerves activated by the second stimulating energy signals.

In accordance with another embodiment, an apparatus is provided for forming an access path through tissue in a patient's body that includes an elongate shaft comprising a proximal end, a distal end sized and configured for introduction into a patient's body to create an access path through tissue; a ring extending around the shaft and movably coupled to the shaft such that the ring is movable axially from a distal position adjacent the distal tip towards the proximal end to a proximal position; a first plurality of stimulating electrodes carried on the ring and configured to contact skin adjacent a puncture site into which the shaft is introduced; and a plurality of sensors spaced apart from one another at fixed locations on the shaft between the proximal and distal ends.

Optionally, the apparatus may also include a controller coupled to the sensors for detecting signals from the first plurality of stimulating electrodes passing through tissue within which the shaft is inserted, the controller configured to process the signals to determine a spatial relationship between the shaft and nerves within the patient's body, e.g., activated by a second set of stimulating elements transmitting stimulating energy signals to activate the nerves. An output device may also be provided for presenting information related to the spatial relationship between the shaft and the activated nerves.

In accordance with still another embodiment, a method is provided for performing a procedure at a target site within a patient's body that includes coupling a first set of stimulating elements to the patient's body to selectively activate nerves adjacent the target site; inserting a distal end of a shaft of an access device into the patient's body from an access site towards the target site such that a second set of stimulating elements on the shaft contact skin of the patient's body adjacent the access site; activating the second set of stimulating elements to deliver stimulating energy into the patient's body; and obtaining signals from the first and second sets of stimulating elements using a plurality of sensors spaced apart from one another on the shaft via tissue surrounding the shaft and the sensors. Information regarding a spatial relationship between the shaft and the nerves activated by the first set of stimulating elements may be presented, e.g., on a display, to guide introduction of the distal end of the shaft to the target site while avoiding contact with the activated nerves.

In accordance with yet another embodiment, a method is provided for performing a medical procedure at a target site within a patient's body that includes coupling one or more stimulating elements to the patient's body at one or more predetermined locations that correspond with one or more nerves that have pathways that pass in or near the target site; delivering energy via the stimulating elements to stimulate the one or more nerves; inserting a distal end of a surgical apparatus into an access site in the patient's skin; using one or more sensors on the surgical apparatus to obtain evoked responses from the one or more stimulated nerves; determining a spatial relationship between the surgical apparatus and the one or more stimulated nerves based at least in part on the evoked responses; and advancing the distal end through tissue towards the target site based at least part on the spatial relationship.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
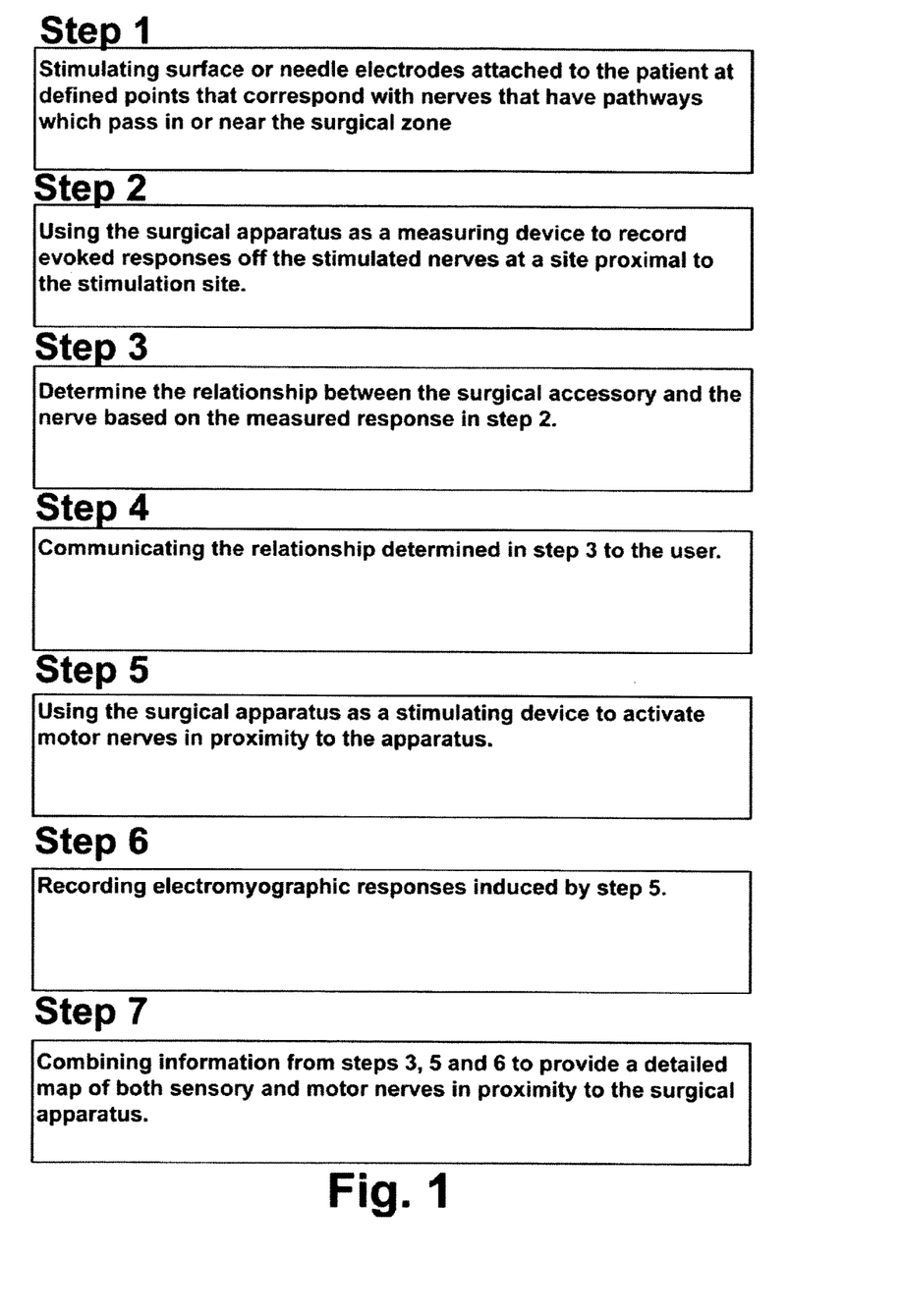
FIG. 1 is a flow chart illustrating exemplary steps of a method for using a neurophysiology-based surgical system.

Turning to the drawings, FIG. 1 shows an exemplary embodiment of a method for surgical access using electrophysiology to provide information on the location of neural elements when creating a surgical access channel. The flowchart outlines an exemplary method according to a first embodiment, which may include the following steps 1-4, and optionally steps 5-6. In Step 1, stimulating surface or needle electrodes may be attached to the patient at defined points that correspond with nerves that have pathways that pass in or near the surgical zone. In Step 2, a surgical apparatus, e.g., a surgical access device, as described elsewhere herein, may be used as a measuring device to record evoked responses off the stimulated nerves at a site proximal to the stimulation site. In Step 3, the spatial relationship between the surgical accessory and the nerve may be determined based at least in part on the measured response in step 2. In Step 4, the spatial relationship determined in Step 3 may be communicated to the user, e.g., on a display, as described elsewhere herein.

In Step 5, optionally, the surgical apparatus may also have stimulating electrodes at various points on the surface and tip of the apparatus. In Step 6, electromyographic activity generated by the stimulus current in Step 5 may be detected by electrodes placed at the patient's extremities, e.g., near the activated muscles. Optionally, in Step 7, the information from steps 5 and 6 may be combined with the data from Step 3 to provide a detailed map of both sensory and motor nerves in proximity to the surgical apparatus.

Figure 4:
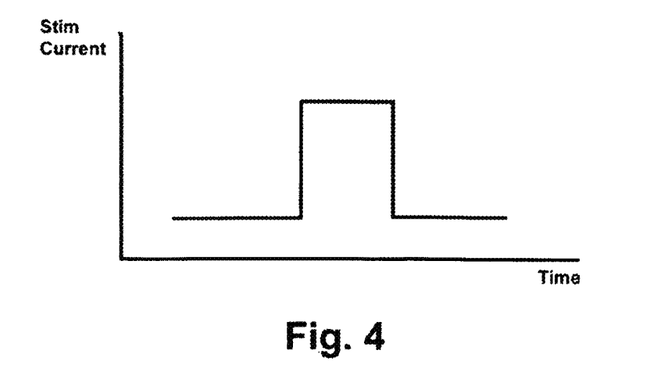
FIG. 4 is a graph illustrating an exemplary plot of a stimulation current capable of eliciting an action potential in an underlying sensory nerve when stimulated in the periphery by either a surface or needle electrode.

The step of stimulating the peripheral nerves generally involves placement of one or more, e.g., a plurality of, electrodes on the patient in the distribution of nerves that follow pathways that potentially take them near the site of the surgical access channel. The sensory nerve pathways are well defined (some inherent variation exists from person to person, but these variations may be overcome by stimulating in patterns that cover most such variations). For example, as shown in FIG. 4, a substantially constant current square wave electrical pulse may be delivered through the electrode(s) to the underlying sensory or mixed (e.g., motor and sensory) nerve in close physical proximity to the electrode(s).

The variables of stimulus intensity and/or pulse width duration may be adjustable by the user, e.g., using a controller coupled to the electrode(s) within the surgical apparatus or external the surgical apparatus (not shown), to deliver an optimal stimulus. The optimal stimulus is defined as that which is adequate to elicit an action potential (nerve activation) in the underlying nerve. This action potential by the artificial electrical stimulus travels up the natural pathway of the nerve to the central nervous system (spinal cord and brain). The stimulated nerve(s) are chosen such that they represent the nerves further upstream that are closest to the planned surgical access channel.

By way of example, for lateral surgical approaches to gain access to the lumbar vertebrae levels L4 and L5 and sacral vertebral level S1, the surgical channel may pass through the psoas muscle and pass near the lumbosacral plexus, which is sometimes injured during this surgical approach using conventional procedures. The first step of the method shown in FIG. 1 may involve stimulating sensory nerves at the distribution on the lower limbs that cover the lumbar L4, L5, and sacral S1 nerve root levels. In addition, several levels above and/or below this region may also be stimulated, e.g., to account for any inherent anatomical variations across individuals. Electrical stimulation may provide an exemplary method for stimulating peripheral sensory nerves, but thermal, tactile, and/or magnetic stimulation methods may also be used in this step to accomplish the same goal of activating the nerve.

Figure 2:
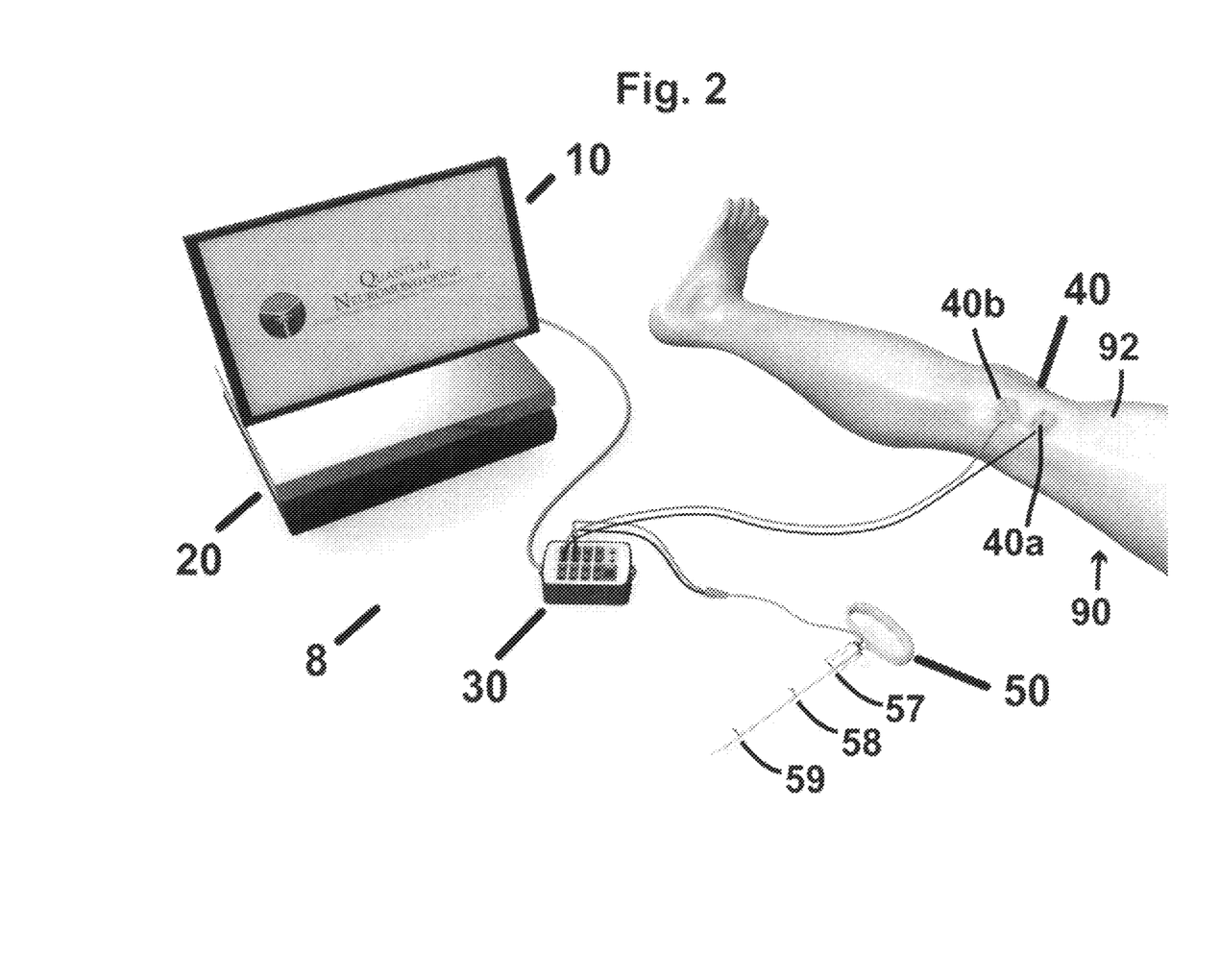
FIG. 2 is a perspective view of an exemplary embodiment of a surgical system that uses evoked nerve responses to determine nerve proximity and direction to surgical instruments used to access a surgical target site.
Figure 3:
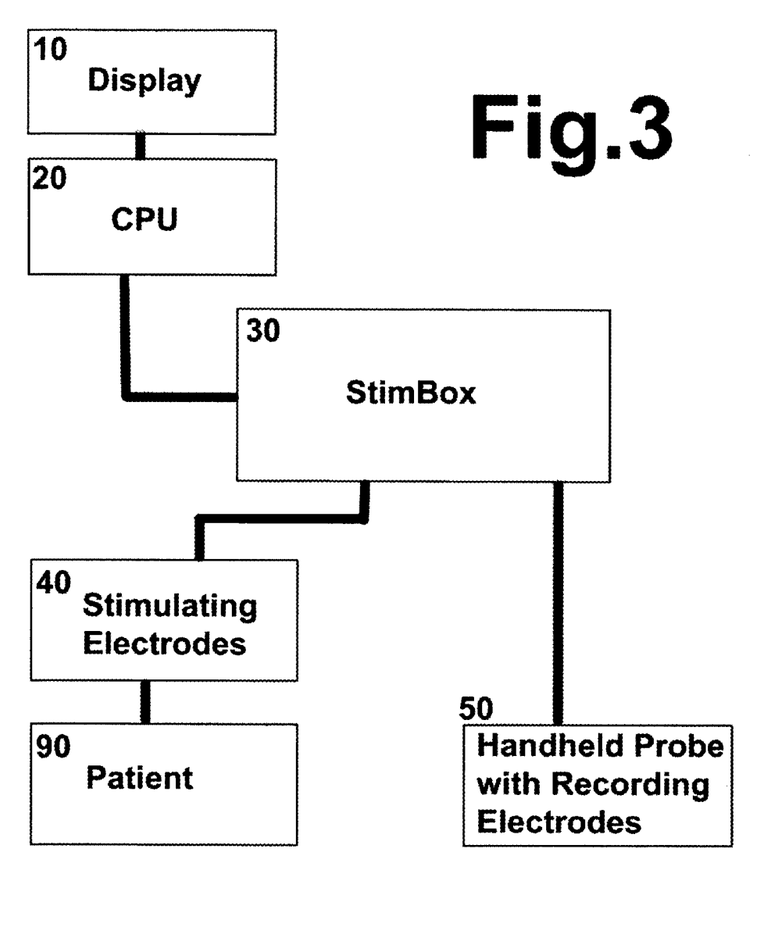
FIG. 3 is a block diagram of the surgical system shown in FIG. 2.
Figure 7:
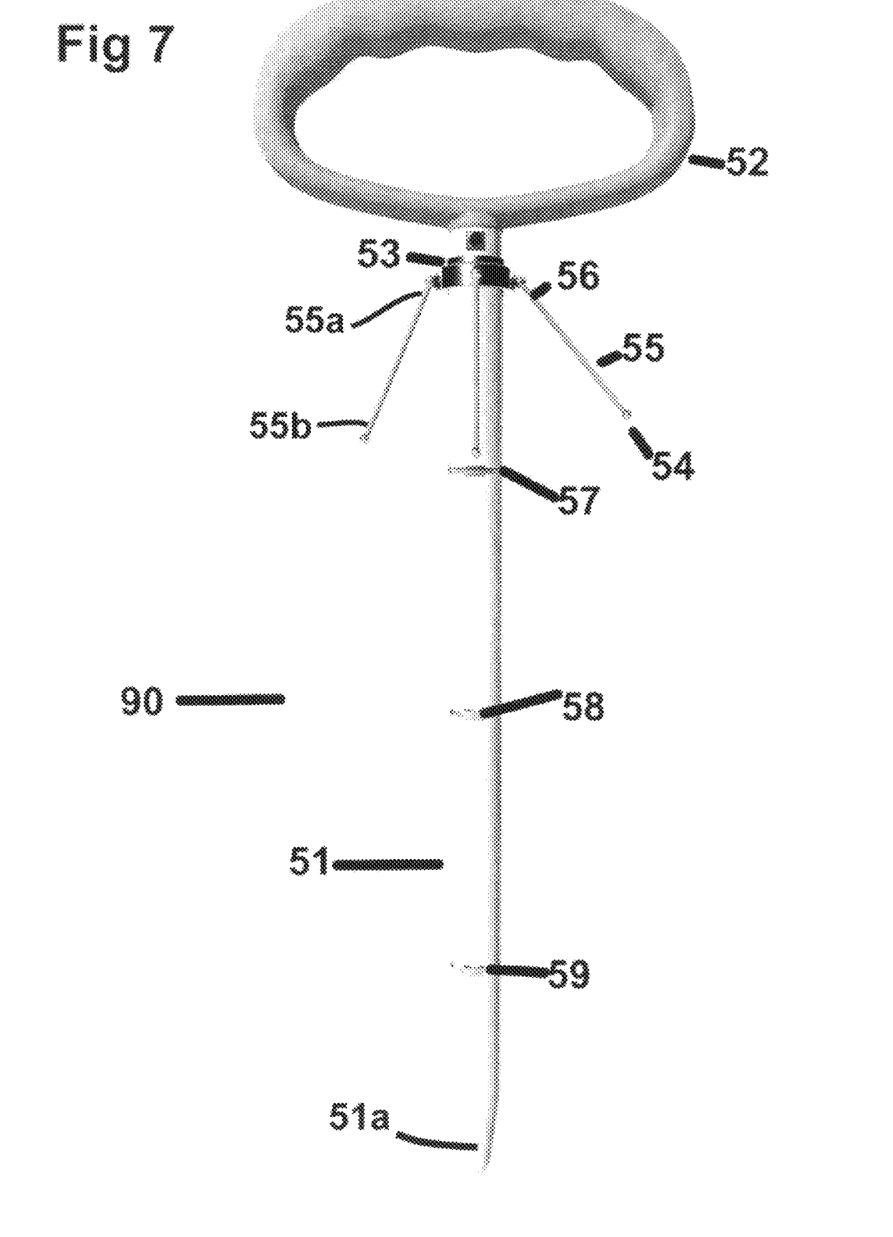
FIG. 7 is a side view of an exemplary embodiment of a surgical access system.

FIGS. 2 and 3 illustrate an exemplary surgical system 8 that may be provided to perform a procedure within a patient's body, e.g., shown in FIG. 7, such as the methods described elsewhere herein. Generally, the system 8 includes a display 10, a controller 20, a stimulation box 30, one or more stimulating electrodes 40, and a surgical or access apparatus 50. The display 10 may be a high resolution graphical display 10 that conveys relevant numerical and/or graphical information about the surgical apparatus 50, e.g., its relation to the patient's body 90, its relation to the nerve(s), and/or its relation to other anatomical landmarks (not shown), e.g., as shown in FIG. 7 and described further elsewhere herein. The controller 20 may be coupled to the display 10, the stimulation box 30, and/or components of the system 8, as desired, e.g., using one or more cables.

Generally, the controller 20 may include one or more components, e.g., a CPU, memory, differential amplifier, signal averager, and analog to digital converter (not shown), e.g., housed in a single unit, as shown in FIG. 2. The stimulation box 30 may take an alternating current input from a power source (not shown, e.g., contained within the box 30 itself or the controller 20) and output square wave direct current pulses or other stimulating signals through the stimulating electrodes 40 that may be plugged into or otherwise coupled to the box 30. The stimulating electrodes 40 may be attached to the surface of the skin of a patient 90, e.g., by one or more of an adhesive, one or more straps (not shown), and the like, and activated to deliver an electrical (and/or magnetic, thermal or tactile) stimulus through the electrode(s) 40 to the underlying nerve(s). The surgical apparatus 50 may include one or more recording electrodes or sensors 57-59 and/or may be configured to create the surgical channel in the patient's body 90, as described elsewhere herein. In addition or alternatively, other sensors may be provided on the shaft 51, e.g., in addition to or instead of the electrodes 57-59, e.g., one or more magnetic sensors and the like (not shown).

In an exemplary embodiment, the set of stimulating electrodes 40 may include first and second electrodes, e.g., providing an anode and a cathode for each nerve stimulated, and a common ground electrode for any number of nerves stimulated. For example, as shown in FIG. 2, each of the anode and cathode may be a patch electrode 40a, 40b attached to the patient's skin 92, e.g., using an adhesive, one or more straps (not shown), and the like. Alternatively, the anode and cathode may be provided on a needle electrode (not shown) that includes a sharpened tip that may be inserted through the skin 92 at desired locations.

The electrodes 40 may be used to deliver electrical energy to stimulate the nerves underlying the skin or otherwise adjacent the electrodes 40. Alternatively, the stimulation of the underlying peripheral nerves may be accomplished by magnetic stimulation, either using single or repetitive pulses from a generator (not shown) placed against the skin 92, which in turn may induce a current in the underlying nerve, which acts as a conductor. In another alternative, the peripheral nerves may be stimulated by thermal energy, such as, by way of example only, a laser or other generator (not shown) directed at or placed against the skin 92. In yet another alternative, the peripheral nerves may be stimulated by mechanical stimulation that produce vibratory or proprioceptive stimulation of the nerves, e.g., using an ultrasound transducer or other device (not shown) placed against the patient's skin 92.

Figure 5:
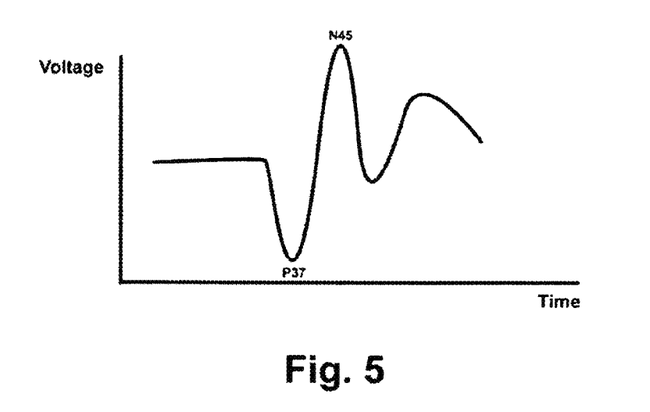
FIG. 5 is a graph illustrating an exemplary evoked potential response at the recording site (e.g., by a surgical apparatus).

FIGS. 4 and 5 illustrate exemplary signals that may be used with the apparatus and methods herein, namely an electrical stimulation signal (shown in FIG. 4), e.g., delivered using the electrodes 40 in FIG. 2, and a resulting response evoked by the stimulation signal after undergoing signal processing (shown in FIG. 5). In particular, FIG. 5 depicts an exemplary response signal that may be detected by the electrodes 57-59 of the apparatus 50, e.g., after it has undergone signal processing, such as amplification, filtering, analog to digital conversion and/or averaging.

By way of example only, the stimulation signal may be a stimulation current of user-adjusted intensity and/or pulse width duration output monophasic pulses in an adjustable frequency of stimulation. The variables of intensity, pulse width, and/or frequency may be optimized to elicit an action potential in an underlying or nearby nerve. The nerve is typically a sensory nerve but alternatively may be a mixed nerve (e.g., with both sensory and motor nerve fibers travelling in the same nerve).

An action potential occurs when the current generated by the stimulation electrode(s) 40 creates a change in voltage of the area surrounding the nerve. This voltage change near the nerve cell membrane causes voltage gated sodium channels to activate and allows the influx of positively charged sodium ions, which depolarize the cell. This depolarization then travels as an action potential along the course of the nerve back towards the spinal cord. At any point along that propagating action potential, a recording electrode that detects voltage changes may be placed and record the signal as it passes near the electrode. These electrical potentials generated by individual nerves are generally very small in signal strength and various signal processing techniques are utilized to improve the signal to noise ratio.

Figure 6:
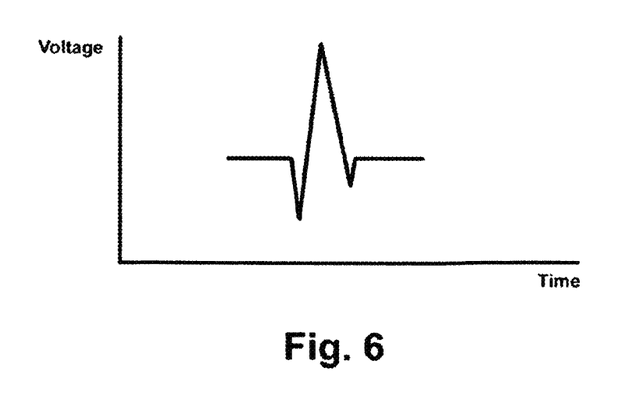
FIG. 6 is a graph illustrating an exemplary compound muscle action potential response recorded from target muscle(s).

FIG. 6 depicts an exemplary response signal of an electromyographic compound action muscle potential, elicited from stimulation of the motor nerve from the surgical apparatus itself, and recorded downstream through the natural orthodromic response of the activated motor nerve.

FIG. 7 illustrates the handheld portion of an exemplary surgical apparatus 50 that may be included in the system 8 shown in FIG. 2. The apparatus 50 may be used by a surgeon or other user, e.g., to create an access channel to a surgical site of interest, e.g., in order to perform a surgical or other procedure at the site. Generally, the apparatus 50 includes an elongate shaft 51 terminating in a distal tip 51a (e.g., having a tapered shape including a sharpened, rounded, or blunt tip), a handle 52 on a proximal end of the shaft 51, and a plurality of electrodes or sensors 54, 57-59. The shaft 51 may be substantially rigid, semi-rigid, and/or malleable, e.g., to facilitate inserting the shaft 51 into a patient's body 90. The shaft 51 may have a desired length, e.g., between about ten and forty centimeters (10-40 cm), which may be fixed or may be adjustable, e.g., by providing two or more telescoping segments (not shown) for the shaft 51. Although three electrodes 57-59 are shown, it will be appreciated that fewer (i.e., two) or more (e.g., four, five, six, or more) electrodes may be provided spaced apart from one another along the shaft 51. Each electrode 57-59 may be a ring array including a plurality of discrete recording electrode units spaced apart from one another, e.g., by about three to five millimeters (3-5 mm), which may serve as either the cathode or the anode of the bipolar recording array.

For example, as shown in FIG. 7, after the surgeon has used a scalpel to create a small incision in the patient's skin 92 that would allow the best access to create a channel to a target surgical site, the distal tip 51a of the shaft 51 may be inserted into the incision. The distal tip 51a may be pointed or otherwise shaped to allow for blunt dissection through adipose, connective tissue, and/or muscle to reach the target site. The user may control advancement of the apparatus 50 into the patient's body 90 by holding the handle 52, which may allow adequate leverage and control. Alternately, the apparatus 50 may be inserted into an existing channel created by other devices that provide the ability to visualize the access channel, with the apparatus 50 used to verify nerve proximity once the channel has been created.

The shaft 51 may include a ring 53 surrounding the shaft 51, which may be movable longitudinally along at least a portion of the length of the shaft 51, e.g., along a track in the shaft 51 and/or guided by one or more gear elements on the shaft 51 and/or ring 53 (not shown). The ring 53, in turn, may carry a plurality of stimulating electrodes 54, e.g., four ball-tipped monopolar electrodes on the end of arms 55 coupled to the ring 53. The arms 55 may be substantially rigid and pivotally or otherwise movably coupled to the ring 53, e.g., such that the electrodes 54 may be displaced outwardly away from the shaft 51 during use, e.g., in one or more or two or more degrees of freedom. For example, the arms 55 may include first ends 55a pivotally coupled to the ring 53 at hinged joints 56 and second free ends 55b, each free end 55b carrying a respective stimulating electrode 54, e.g., having a ball or other atraumatic shape. The stimulating electrodes 54 may be coupled to the controller 20 (shown in FIG. 2) for delivering appropriate signals into the patient's skin 92. Alternatively, other stimulation elements may be used, such as magnetic, acoustic, thermal or other generators (not shown).

In an exemplary initial configuration, the ring 53 may be disposed in a starting or distal position near the distal tip 51a of the shaft 51 (not shown) with the arms 55 positioned immediately adjacent the shaft 51, e.g., substantially parallel to the shaft 51, with the electrodes 54 adjacent or beyond the distal tip 51. As the distal tip 51 is advanced into tissue towards a target site, the ball-tipped electrodes 54(4) may come in contact with the skin 92 of the patient's body 90. As the shaft 51 is further advanced into the patient's body 90, the force causes the ball tip electrodes 54 first to slide away from the shaft 51 pivoting the arms 55 outwardly away from the shaft 51 adjacent the patient's skin 92. When the arms 55 are substantially perpendicular, e.g., at ninety degrees (90°) relative to the ring 53, the ring 53 may contact the skin 92 and get pushed proximally along the shaft 51 from the distal tip 51a towards the handle 52 as the shaft 51 continues to enter the patient's body 90. The ball-tipped electrodes 54 serve to generate a stimulating current, which in turn may be recorded at recording electrode arrays 57, 58, 59 spaced apart on the shaft 51.

The recording electrodes 57-59 may be activated sequentially, e.g., after passing through the ring 53 of the apparatus 50 to ensure they are only active inside the patient's body 90, which in turn may eliminate extraneous electrical noise and artifact. For example, a sensor (not shown) on the apparatus 50 may detect the position of the ring 53 and the controller 20 may activate each electrode 57-59 only when the sensor confirms that the respective electrode 57-59 is positioned distally beyond the ring 53 and therefore inserted into the patient's body 90. In an exemplary embodiment, electrode array 57 may include a first plurality of electrodes spaced apart from one another in a ring around the shaft 51 at a first location, e.g., adjacent the distal tip 51a of the shaft 51, electrode array 58 may include a second plurality of electrodes also arranged in a ring configuration at a second location further from the distal tip 51a and closer to the handle 52, e.g., at a midpoint on the shaft 51, and electrode array 59 may include a third plurality of electrodes also arranged in a ring configuration at a third location furthest from the distal tip 51a and closest to the handle 52.

In an exemplary method, electrode array 57 may be activated first, a threshold measurement may be recorded with stimulating electrical pulses from the ball-tipped electrodes 54 at the surface of the skin 92. Similarly, threshold measurements may be obtained as each of the electrode arrays 58 and 59 pass through the skin 92 into the patient's body 90. The obtained measured thresholds, being at known distances relative to the skin 92 and the shaft 51, are used as reference values to determine the distance and position in three dimensional space of the elicited nerve responses recorded from the same array of electrodes.

Figure 8:
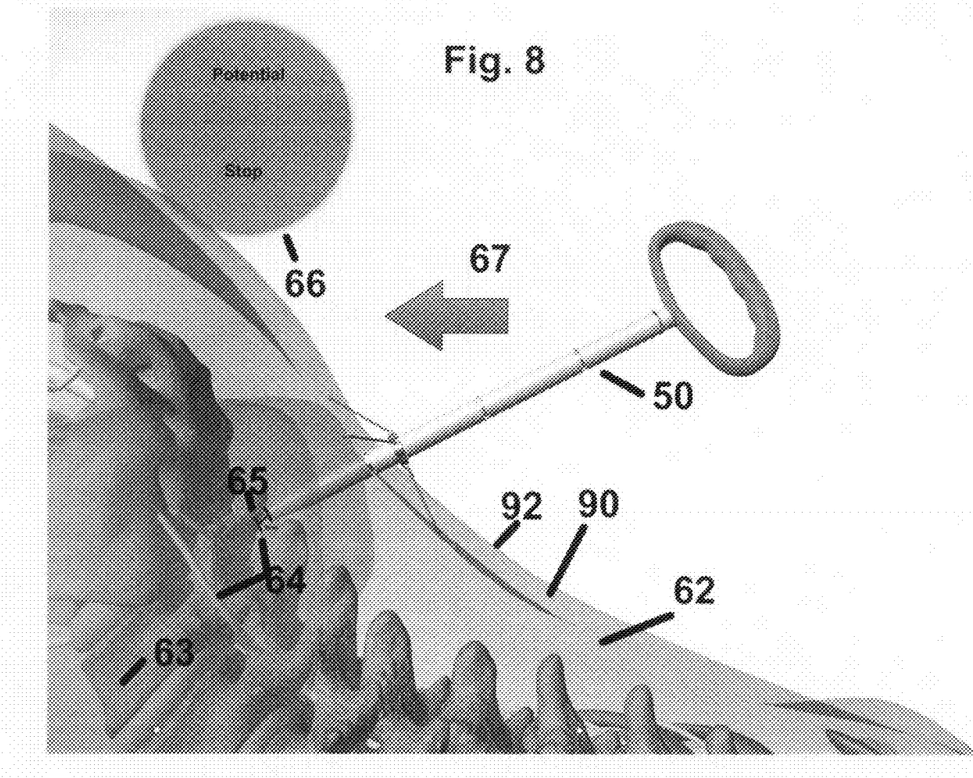
FIG. 8 is an exemplary screen display illustrating one embodiment of the graphical display of the relation of the surgical apparatus to the nerve.

FIG. 8 illustrates an exemplary graphical display of the surgical apparatus 50, e.g., which may be presented on a display such as the display 10 shown in FIG. 2. The display 10 may either be a standalone unit dedicated to the function of the surgical apparatus 50 or may integrate with other imaging displays to provide accurate anatomical landmarks through imaging studies. As shown, the surgical apparatus 50 is being inserted into the patient's body 90 to create a surgical access channel. Anatomical landmarks (e.g., 62, 63, 64) may be stylized and displayed graphically. The image presented on the display 10 may include an actual image of the patient's body 90 or a graphical image representing the body 90, showing that the apparatus 50 is channeling through the tissue of the patient's body 90, depending on the imaging data the specific type of tissue (muscle, adipose, fat) being displayed. For example, the vertebrae 63 may be stylized, but may be correlated with specific radiographic imaging data to provide an accurate representation.

The nerve(s) 64 course and position relative to the probe portion of the handheld apparatus may be accurately derived by the measurement capabilities of the apparatus 50 and system 8, and the nerve position may be represented both graphically and/or as a distance to the closest point of the nerve relative to the shaft 51 of the apparatus 50, e.g., as represented by distance 65. Optionally, visual aids may be provided on the display 10 (in addition to or instead of the graphical display), e.g., in the form of clearly marked graphical icons 66, 67, which may facilitate the user inserting the shaft 51 while avoiding contact with the nerves identified using the system 8. The data acquisition stage of the apparatus 50 may be optimized when the shaft 51 is advanced through the tissue in intervals.

For example, the user may be given a clear graphical display 66, e.g., of either 'Proceed' which is highlighted in green or 'Stop' which is highlighted in red. The user may use this information to guide the insertion of the apparatus 50 into the patient's body 90. Optionally, a three-dimensional graphical arrow 67 or other graphic may be included that provides guidance to the user, e.g., showing the angle of direction that the shaft 51 of the apparatus 50 should be directed toward, e.g., in order to gain the greatest distance from identified nerve roots.

Once the distal tip 51a reaches the target site, an access sheath or other device (not shown) may be introduced over or through the shaft 51 to provide access to the target site, and then the shaft 51 may be removed leaving the access sheath in position. One or more surgical or other instruments (also not shown) may then be directed through the access sheath to perform a procedure at the target site. Once the procedure is completed, the instruments and access sheath may be removed and the puncture in the skin closed. Thus, the apparatus 50 and system 8 may create a safe access path for such access devices and/or instruments while avoiding contact and/or damage to nerves in close proximity to the access path.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. An apparatus for forming an access path through tissue in a patient's body, comprising:
   an elongate shaft comprising a proximal end, a distal end sized and configured for introduction into a patient's body to create an access path through tissue;
   a ring extending around the shaft and movably coupled to the shaft such that the ring is movable axially from a distal position adjacent the distal tip towards the proximal end to a proximal position;
   a first plurality of stimulating electrodes carried on the ring and configured to contact skin adjacent a puncture site into which the shaft is introduced; and
   a plurality of sensors spaced apart from one another at fixed locations on the shaft between the proximal and distal ends.

2. The apparatus of claim 1, further comprising a controller coupled to the sensors for detecting signals from the first plurality of stimulating electrodes passing through tissue within which the shaft is inserted, the controller configured to process the signals to determine a spatial relationship between the shaft and nerves within the patient's body.

3. The apparatus of claim 2, further comprising an output device for presenting information related to the spatial relationship between the shaft and the nerves.

4. A method for performing a procedure at a target site within a patient's body, comprising:
   coupling a first set of stimulating elements to the patient's body to selectively activate nerves adjacent the target site;
   inserting a distal end of a shaft of an access device into the patient's body from an access site towards the target site such that a second set of stimulating elements on the shaft contact skin of the patient's body adjacent the access site;
   activating the second set of stimulating elements to deliver stimulating energy into the patient's body;
   obtaining signals from the first and second sets of stimulating elements using a plurality of sensors spaced apart from one another on the shaft via tissue surrounding the shaft and the sensors; and
   presenting information regarding a spatial relationship between the shaft and the nerves activated by the first set of stimulating elements to guide introduction of the distal end of the shaft to the target site while avoiding contact with the activated nerves.

5. The method of claim 4, further comprising performing a medical procedure at the target site.

6. The method of claim 5, wherein performing a medical procedure comprises:
   introducing a distal end of a tubular member from the access site to the target site using the shaft;
   removing the shaft from the patient's body while leaving the tubular member distal end at the target site; and
   introducing one or more instruments through the tubular member to perform a procedure at the target site.

7. The method of claim 4, wherein the first set of stimulating elements comprise a plurality of patch electrodes and wherein coupling the first set of stimulating elements to the patient's body comprises attaching the plurality of patch electrodes to the patient's skin adjacent nerves to be activated.

8. The method of claim 4, wherein the first set of stimulating elements comprise a needle electrode and wherein coupling the first set of stimulating elements to the patient's body comprises inserting the needle electrode through the patient's skin into tissue adjacent nerves to be activated.

9. The method of claim 4, wherein the first set of stimulating elements are coupled to the patient's leg and wherein the target site is adjacent the patient's spine.

10. A system for forming an access path through tissue in a patient's body, comprising:
    an elongate shaft comprising a proximal end, a distal end sized and configured for introduction into a patient's body to create an access path through tissue, a first plurality of stimulating electrodes movable on the shaft between a distal position and a proximal position and configured to contact skin of the patient's body into which the shaft is introduced, and a plurality of sensors fixed on the shaft and spaced apart from one another between the proximal and distal ends;
    a second plurality of electrodes configured to be coupled to a patient's body to deliver stimulating energy to one or more nerves within the patient's body;
    a controller coupled to the first plurality of stimulating electrodes for delivering first stimulating energy signals to the first plurality of stimulating electrodes and coupled to the second plurality of stimulating electrodes for delivering second stimulating energy signals to nerves within the patient's body, the controller coupled to the sensors for detecting signals from the first and second plurality of stimulating electrodes passing through tissue within which the shaft is inserted and process the signals to determine a spatial relationship between the shaft and nerves within the patient's body activated by the second stimulating energy signals; and
    an output device for presenting information related to the spatial relationship between the shaft and the nerves activated by the second stimulating energy signals.

11. The system of claim 10, wherein the first plurality of stimulating electrodes are mounted on a ring that is slidable along the shaft.

12. The system of claim 11, wherein the first plurality of stimulating electrodes are mounted on arms pivotally coupled to the ring such that the arms and electrodes are spaced apart around a perimeter of the ring.

13. The system of claim 12, wherein the first plurality of stimulating electrodes provide substantially atraumatic tips for the arms.

14. The system of claim 10, wherein the second plurality of stimulating electrodes comprise patch electrodes.

15. The system of claim 10, wherein the second plurality of stimulating electrodes comprise a needle electrode.

16. The system of claim 10, wherein the second plurality of stimulating electrodes comprise an anode and a cathode.

17. The system of claim 10, wherein each sensor comprises a plurality of electrodes spaced apart around a perimeter of the shaft.

18. The system of claim 17, wherein the plurality of sensors comprise three or more sensors spaced apart from one another along the shaft by predetermined distances.

19. The system of claim 10, wherein the plurality of sensors are configured for acquiring electrical voltage potentials generated by the nerves activated by the second plurality of stimulating electrodes, the controller configured to process the voltage potentials to determine a spatial relationship between the shaft and the activated nerves.

* * * * *